US009789216B2

(12) United States Patent
Berentsveig et al.

(10) Patent No.: US 9,789,216 B2
(45) Date of Patent: Oct. 17, 2017

(54) SYNERGISTIC DISINFECTION ENHANCEMENT

(71) Applicant: Saban Ventures Pty Limited, Alexandria, New South Wales (AU)

(72) Inventors: Vladimir Berentsveig, Alexandria (AU); Dipika Patel, Alexandria (AU)

(73) Assignee: Saban Ventures Pty Limited, Lane Cove, New South Wales (AU)

( * ) Notice: Subject to any disclaimer, the term of this patent is extended or adjusted under 35 U.S.C. 154(b) by 0 days.

(21) Appl. No.: 14/651,595

(22) PCT Filed: Dec. 13, 2013

(86) PCT No.: PCT/AU2013/001462
§ 371 (c)(1),
(2) Date: Jun. 11, 2015

(87) PCT Pub. No.: WO2014/089632
PCT Pub. Date: Sep. 19, 2014

(65) Prior Publication Data
US 2015/0314025 A1 Nov. 5, 2015

(30) Foreign Application Priority Data
Dec. 14, 2012 (AU) ................. 2012905482

(51) Int. Cl.
*A61K 33/40* (2006.01)
*A01N 25/00* (2006.01)
*A61L 2/18* (2006.01)
*A01N 59/00* (2006.01)
*A01N 37/16* (2006.01)

(52) U.S. Cl.
CPC .............. *A61L 2/186* (2013.01); *A01N 37/16* (2013.01); *A01N 59/00* (2013.01)

(58) Field of Classification Search
None
See application file for complete search history.

(56) References Cited

U.S. PATENT DOCUMENTS

| 1,535,529 | A | 4/1925 | Hopkins |
| 2,454,541 | A | 11/1948 | Bock et al. |
| 3,341,418 | A | 9/1967 | Moses et al. |
| 3,488,287 | A | 1/1970 | Seglin et al. |
| 3,554,289 | A | 1/1971 | Webb |
| 3,708,431 | A | 1/1973 | Prussin |
| 4,051,059 | A | 9/1977 | Bowing et al. |
| 4,522,738 | A | 6/1985 | Magid et al. |
| 4,743,447 | A | 5/1988 | Le Rouzic et al. |
| 5,154,917 | A | 10/1992 | Ibraham et al. |
| 5,168,048 | A | 12/1992 | Quax |
| 5,269,959 | A | 12/1993 | Schreibman |
| 5,314,687 | A | 5/1994 | Oakes et al. |
| 5,344,652 | A | 9/1994 | Hall, II et al. |
| 5,480,575 | A | 1/1996 | Altieri et al. |
| 5,489,706 | A | 2/1996 | Revell |
| 5,545,374 | A | 8/1996 | French et al. |
| 5,643,862 | A | 7/1997 | Jones et al. |
| 5,656,302 | A | 8/1997 | Cosentino et al. |
| 5,804,546 | A | 9/1998 | Hall |
| 5,900,256 | A | 5/1999 | Scoville, Jr. et al. |
| 6,080,712 | A | 6/2000 | Revell et al. |
| 6,168,808 | B1 | 1/2001 | Hamon Godin et al. |
| 6,511,546 | B1 | 1/2003 | Bivins et al. |
| 6,514,509 | B2 | 2/2003 | Tabasso |
| 6,583,103 | B1 | 6/2003 | Klinkhammer |
| 6,589,565 | B1 | 7/2003 | Richter et al. |
| 6,699,828 | B1 | 3/2004 | De Buzzaccarini et al. |
| 6,726,936 | B1 | 4/2004 | Asano et al. |
| 6,767,874 | B2 | 7/2004 | Gonzalez |
| 7,056,536 | B2 | 6/2006 | Richter et al. |
| 7,189,385 | B2 | 3/2007 | Montgomery |
| 7,205,000 | B2 | 4/2007 | Einziger |
| 7,271,137 | B2 | 9/2007 | Tucker et al. |
| 8,012,411 | B1 | 9/2011 | Betty et al. |
| 8,377,421 | B2 | 2/2013 | Giniger |
| 8,546,120 | B2 | 10/2013 | Dicosimo et al. |
| 8,969,283 | B2 | 3/2015 | Kaiser et al. |
| 2003/0129254 | A1 | 7/2003 | Yasuhara et al. |
| 2005/0036904 | A1 | 2/2005 | Kajander et al. |
| 2005/0282722 | A1 | 12/2005 | McReynolds et al. |

(Continued)

FOREIGN PATENT DOCUMENTS

AU 701927 B2 6/1995
CN 102090393 A 6/2011
(Continued)

OTHER PUBLICATIONS

Machine Translation for EP 1 293 215 B1; downloaded Aug. 27, 2015.*
Multitrope (aka Monafaz) 1214 MSDS; downloaded Aug. 27, 2015.*
Genapol EP 2564 MSDS product data sheet; Clariant; downloaded Aug. 27, 2015.*
Chemical Abstracts, vol. 101, No. 4, Jul. 23, 1984, p. 102, No. 25407e, Columbus, Ohio US; Kasei K.K.: "Sprayable Foaming Cleaning Compositions" & Jpn. Kokai Tokkyo Koha JP 58,191,800/ 83,191,8007, 1 page.
"pH Curves and Indicators", 2003, Nigel Saunders N-ch4-05, 3 pages.
The Merck Index, Encyclopedia of Chemicals, Drugs and Biologicals, 6601. Octoxynol, Windholz et al., Eds., Tenth Edition, Copyright 1983, 4 pages.

(Continued)

Primary Examiner — Jeffrey T. Palenik
(74) Attorney, Agent, or Firm — Senniger Powers LLP

(57) ABSTRACT

An aqueous disinfectant solution comprising peroxyacetic acid and a surfactant such as a polyoxyethylene alkyl ether phosphate, (polyethylene glycol p-(1,1,3,3-tetramethylbutyl)-phenyl ether) or cocoamidopropylamino oxide. The solution is preferably adjusted to provide a pH in the range 5-8 by a pH adjusting agent such as a phosphate buffer; hydroxide; carbonate; bicarbonate; a combination of carbonate and hydroxide; or a combination of carbonate and bi carbonate.

26 Claims, No Drawings

(56) References Cited

U.S. PATENT DOCUMENTS

| | | |
|---|---|---|
| 2006/0198797 A1 | 9/2006 | Giniger |
| 2006/0204453 A1 | 9/2006 | Giniger |
| 2006/0229226 A1 | 10/2006 | Giniger et al. |
| 2007/0161243 A1 | 7/2007 | Mellies |
| 2007/0166398 A1 | 7/2007 | Bobbert |
| 2007/0185000 A1 | 8/2007 | Zushi et al. |
| 2007/0258915 A1 | 11/2007 | Kielbania |
| 2009/0061017 A1* | 3/2009 | Pedersen .......... A01N 37/16 424/616 |
| 2009/0285871 A1 | 11/2009 | Cunningham et al. |
| 2009/0324508 A1 | 12/2009 | Bobbert |
| 2010/0068295 A1* | 3/2010 | Bobbert ............ A01N 59/00 424/616 |
| 2010/0196503 A1 | 8/2010 | Heisig et al. |
| 2010/0196505 A1 | 8/2010 | Kaiser et al. |
| 2010/0227000 A1 | 9/2010 | Ames et al. |
| 2010/0294987 A1 | 11/2010 | Kater |
| 2011/0081693 A1 | 4/2011 | Dicosimo et al. |
| 2011/0085991 A1 | 4/2011 | Giniger |
| 2012/0171301 A1 | 7/2012 | Koenig et al. |
| 2012/0219636 A1 | 8/2012 | Li et al. |

FOREIGN PATENT DOCUMENTS

| | | | |
|---|---|---|---|
| CN | 102964285 A | 3/2013 | |
| EP | 0745665 A2 | 12/1996 | |
| EP | 0752466 A1 | 1/1997 | |
| EP | 0733097 B1 | 10/1998 | |
| EP | 1123655 A1 | 8/2001 | |
| EP | 1829558 A1 | 9/2007 | |
| EP | 1293215 B1 | 11/2007 | |
| EP | 2436265 A2 | 4/2012 | |
| FR | EP 1 293 215 B1 * | 4/2007 | ........... A61L 12/124 |
| GB | 2293157 A | 3/1996 | |
| JP | S58191800 A | 11/1983 | |
| JP | S5966499 A | 4/1984 | |
| JP | 2003-292996 A | 10/2003 | |
| JP | 2004-285154 A | 10/2004 | |
| JP | 2011-121912 A | 6/2011 | |
| NL | EP 1 987 121 B1 * | 11/2008 | ............ C11D 3/39 |
| WO | 8808667 A1 | 11/1988 | |
| WO | 9116435 A1 | 10/1991 | |
| WO | 9414321 A1 | 7/1994 | |
| WO | 9516023 A1 | 6/1995 | |
| WO | 9619558 A1 | 6/1996 | |
| WO | 98/11777 A1 | 3/1998 | |
| WO | 9833880 A1 | 8/1998 | |
| WO | 9837762 A1 | 9/1998 | |
| WO | 9846715 A1 | 10/1998 | |
| WO | 0078153 A1 | 12/2000 | |
| WO | 2005055963 A2 | 6/2005 | |
| WO | 2006/016145 A1 | 2/2006 | |
| WO | 2006016145 A1 | 2/2006 | |
| WO | 2006089139 A2 | 8/2006 | |
| WO | 2007051957 A1 | 5/2007 | |
| WO | 2007/080187 A1 | 7/2007 | |
| WO | 2008/033206 A1 | 3/2008 | |
| WO | 2008140974 A1 | 11/2008 | |
| WO | 2009027857 A1 | 3/2009 | |
| WO | 2009064856 A1 | 5/2009 | |
| WO | WO 2009/064856 A1 * | 5/2009 | ............ A01N 59/00 |
| WO | 2009/118714 A2 | 10/2009 | |
| WO | 2010102188 A1 | 9/2010 | |
| WO | 2011/008225 A2 | 1/2011 | |
| WO | 2012021520 A1 | 2/2012 | |
| WO | 2012128734 A1 | 9/2012 | |
| WO | 2013096814 A1 | 6/2013 | |

OTHER PUBLICATIONS

TRITON X-100, Product Information Sheet, Sigma-Aldrich, Apr. 21, 1999, 2 pages.

Silocone Antifoams, Antifoam 86/103, Basildon Chemicals, http://www.baschem.co.uk/products/product-type/silicone-antifoams/antifoam-86013/[Sep. 12, 2013 3:52:37 PM], 2 pages.

English Abstract of KR1020080098157A with EPO Machine Translation, 13 pages.

Multitrope (aka Monafax) 1214 MSDS; downloaded Aug. 27, 2015, 1 page.

Genapol EP 2564 MSDS Product Data Sheet; Clariant; downloaded Aug. 27, 2015, 2 pages.

Triton X-100 Surfactant, Product Information Sheet, The Dow Chemical Company, Form No. 119-01882-1207, 2 pages.

International Search Report dated Feb. 28, 2014, in PCT/AU2013/001462, 5 pages.

Written Opinion dated Feb. 28, 2014, in PCT/AU2013/001462, 10 pages.

Extended European Search Report dated Jul. 19, 2016, in European Patent Application No. 13862176.8, 8 pages.

* cited by examiner

SYNERGISTIC DISINFECTION ENHANCEMENT

FIELD OF THE INVENTION

The present invention relates to compositions suitable for use in disinfecting or sterilizing instruments, exposed surfaces or spaces which may be infected with bacteria, fungi, viruses, fungal or bacterial spores, prions, and the like.

BACKGROUND

Any discussion of the prior art throughout the specification should in no way be considered as an admission that such prior art is widely known or forms part of common general knowledge in the field.

BACKGROUND OF THE INVENTION

"Sterilization" has been defined as the process of destroying all microorganisms, spores and their pathogenic products. A 6 log reduction in the amount of such pathogens is generally required to provide a suitable sterility assurance level. "Disinfection" is a similar process, the difference being that it results in a lesser degree of biocidal effect, particularly on bacterial spores. Disinfection is thus easier to achieve than sterilization.

Sterilants or disinfectants are usually liquids and can be applied to articles requiring disinfection or sterilization in a variety of ways. In recent years, the use gas or aerosol dispensing technologies to dispense sterilants or disinfectants has become widespread. Gas or aerosol processes are particularly attractive since they reduce the amount of liquid sterilant or disinfectant used. The primary benefit of using micro volumes of liquid is that rising steps can sometimes be eliminated and drying times are often significantly reduced compared to using say, soaking baths. This shortened cycle time reduces the turnaround time for any given instrument which in turn translates into a much smaller capital outlay is tied up in instruments.

Gas or aerosol processes also tend to be conducted in closed systems, which means that operator safety is also enhanced relative to conventional methods that expose workers to large volumes of open sterilant or disinfectant solutions.

Aerosol based approaches in which nebulisation takes place by ultrasonication of a bulk liquid are known and are a particularly good way to achieve high sterilization efficacies using micro volumes of sterilant.

In recent years there has been a marked increase in the number, variety and levels of resistance of micro-organisms which have been identified as particularly problematic in hospital and medical environments. The use of hydrogen peroxide or peroxyacetic acid as a disinfectant has become greatly preferred in that time. Prior to the 1990s these peroxides were considered too unstable and hazardous to be used.

Peroxyacetic acid is particularly effective against micro-organisms. It is a very broad spectrum germicidal agent, effective against both gram negative and gram positive bacteria, fungi and yeasts and viruses under suitable conditions. It is also considered to be sporicidal. It is efficacious in low concentrations and it remains highly effective even in the presence of relatively high organic loads. The decomposition products of peroxyacetic acid, namely acetic acid, water and oxygen are also environmentally friendly.

Peroxyacetic acid is advantageous over hydrogen peroxide, since, unlike hydrogen peroxide it is not deactivated by microorganisms' catalase or peroxidase. There is also little or no habituation of microorganisms to peroxyacetic acid.

Aqueous peroxyacetic acid solutions are commercially available. Peroxyacetic acid typically exists in equilibrated aqueous mixtures of hydrogen peroxide and acetic acid as represented by the following equation:

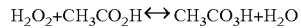

$$H_2O_2 + CH_3CO_2H \leftrightarrow CH_3CO_3H + H_2O$$

One example of such a commercially available peroxyacetic acid solution is Proxitan from Solvay which contains approximately 5% peroxyacetic acid, 7.5% acetic acid and 24% $H_2O_2$. These amounts typify the ratios found in such equilibrated mixtures, namely peroxyacetic acid:acetic acid:hydrogen peroxide in a ratio of 1:1.5:5.

Peroxyacetic acid solutions are quite acidic and are highly corrosive. When using these in the field of sterilization it is usually necessary to add a buffering component to reduce pH to reduce corrosion and to produce a much more generally physiologically acceptable pHs. Phosphate buffers are typically used for this purpose.

It is an object of the present invention to overcome or ameliorate at least one of the disadvantages of the prior art, or to provide a useful alternative.

SUMMARY

According to a first aspect the invention provides an aqueous disinfectant solution comprising:
peroxyacetic acid; and
a surfactant.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

According to a second aspect, the invention provides an aqueous disinfectant solution comprising:
peroxyacetic acid;
a surfactant; and
a buffer to provide a pH in the range 5-8.

According to a third aspect, the invention provides an aqueous disinfectant solution comprising:
peroxyacetic acid;
hydrogen peroxide;
a surfactant; and
a buffer to provide a pH in the range 5-8.

According to a fourth aspect, the invention provides an enhanced aqueous disinfectant solution comprising:
peroxyacetic acid;
hydrogen peroxide;
acetic acid;
a surfactant; and
a buffer to provide a pH in the range 5-8.

Preferably the concentration of peroxyacetic acid is greater than 0.1 wt %, although in alternative embodiments is can be greater than 0.15 wt % or greater than 0.2 wt %. It is generally preferred if the amount of peroxyacetic acid is 0.10 to 0.30 wt %.

Preferably, where hydrogen peroxide is present, the ratio of hydrogen peroxide:peroxyacetic acid is 5:1 or greater, although in alternative embodiments the ratio of hydrogen peroxide:peroxyacetic acid is 10:1 or greater, 15:1 or greater; or even 30:1 or greater.

In one preferred embodiment, the surfactant is an amine oxide. Examples of suitable amine oxides include: cocamidopropylamine oxide (RCONH(CH$_2$)$_3$N(CH$_2$)$_2$→O) where R is a cocoalkyl group; dodecyldimethylamine oxide (C$_{14}$H$_{31}$N→O); ((CH$_2$)$_{13}$(CH$_2$)$_2$N→O), or ((CH$_2$)$_{12-18}$(CH$_2$)$_2$N→O).

In an alternative preferred embodiment, the surfactant is a non-ionic surfactant, such as Triton X-100, (polyethylene glycol p-(1,1,3,3-tetramethylbutyl)-phenyl ether) or Tween-80 (polyethlyene (20) sorbitan monooleate).

In an alternative preferred embodiment, the surfactant is a cationic surfactant. This includes quaternary ammonium compounds such as benzalkonium chloride or hexadecylpyridinium bromide.

In a further alternative preferred embodiment, the surfactant is a phosphate ester based anionic surfactant. Such compounds include polyoxyethylene alkyl ether phosphates, such as those sold by Croda under the trade name Monafax M1214 or Multitrope 1214; phosphate esters (mono- and/or diester of phosphoric acid with aliphatic alcohols of chain length C$_1$-C$_{22}$ and/or aliphatic diols and/or aliphatic polyols of chain length C$_2$-C$_{22}$) such as Hordaphos 1306 or Hordaphos MDGB from Clariant, which is a diester of phosphoric acid with butanol and ethylene glycol respectively; and Excellene T5 NF which is a blend of ethylhexylphosphate ester and alcohol ethoxylate phosphate ester potassium salts, available from Whewell chemical manufacturers.

Preferably, the buffer provides a pH in the range 6-7, most preferably between 5.5 and 6.5.

Preferably the solution is adjusted to provide a pH in the range 5-8 by a pH adjusting agent selected from the group consisting of a phosphate buffer; hydroxide; carbonate; bicarbonate; a combination of carbonate and hydroxide; or a combination of carbonate and bicarbonate.

Preferably the solution is adjusted by a carbonate buffer that comprises hydrogen carbonate anions and hydroxide anions or hydrogen carbonate anions and carbonate anions.

The disinfectant solution may also include a corrosion inhibitor, such as a benzotriazole or urea.

The disinfectant solution may, for preference include an antifoaming agent.

According to a fifth aspect the invention provides a method of disinfection of an article comprising contacting the article with an aqueous disinfectant solution according to the previous aspects.

Preferably the method is carried out in a temperature range of from 15-40° C., more preferably from 20-35° C. and most preferably at ambient temperature.

The time required is preferably that to achieve a resultant load on microorganisms that is acceptable for the intended use of the article. Put alternatively, the time required by the aqueous disinfectant of the present invention to achieve a 6 log reduction in microorganism load at room temperature is preferably less than 5 minutes, or even more preferably less than 4 minutes.

The present invention is applicable both to the disinfection or sterilization of instruments and articles placed in small disinfection chambers, biological safety cabinets, isolators, glove boxes, incubators, materials airlocks and the like. The invention is also applicable for disinfection or sterilization of food containers or the like and manufacturing machinery and is also applicable for the disinfection of very large spaces.

DESCRIPTION

Peroxyacetic acid is generated by the addition of acetic acid to a peroxidising agent such as hydrogen peroxide or a peroxy salt. The most common and inexpensive method used to generate peroxyacetic acid is to use a combination of acetic acid and aqueous hydrogen peroxide, in which case the peroxyacetic acid is in equilibrium with a number of other species as shown:

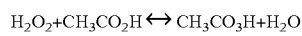

$$H_2O_2 + CH_3CO_2H \leftrightarrow CH_3CO_3H + H_2O$$

As mentioned, the native ratios found in such equilibrated mixtures typically provide peroxyacetic acid:acetic acid:hydrogen peroxide in a ratio of 1:1.5:5. That is, the ratio of the active disinfectant species, peroxyacetic acid and hydrogen peroxide, in such systems is typically around 1:5.

Peroxyacetic acid can also be generated from solid peroxide precursors such as sodium perborate, sodium percarbonate, carbamide peroxide (urea peroxide) or potassium fluoride peroxosolvate in combination with acetic acid to generate peroxyacetic acid. Although slightly more expensive than the acetic acid/hydrogen peroxide approach, these sources of peroxyacetic acid are seen as desirable since they do not include large amounts of hydrogen peroxide, which is regarded as a less potent biocide than peroxyacetic acid.

In some cases, solid peroxide precursors can be used in combination with hydrogen peroxide/acetic acid systems.

Regardless of how it is produced, the pH of peroxyacetic acid is very low, around 2.8. Such a low pH means that it is highly corrosive. Such a low pH is also fundamentally incompatible with systems that are to be used in intimate contact with patients. This means that in order to be used in sensitive medical instruments, it is generally desired that pH is controlled by way of a pH adjusting agent such as a basic agent or buffer. An ideal pH range that will result in minimal corrosion with maximum compatibility for human contact is between about pH 5.5 and pH 7, more particularly between about pH 5.5 and pH 6.5.

Phosphate buffers can be used to control the pH of peroxyacetic acid systems. However, other common bases, such as hydroxide or carbonate, have also been used to adjust the pH of peroxyacetic acid.

In buffers comprising hydrogen carbonate anions and hydroxide anions, the molar ratio of hydrogen carbonate:hydroxide is about 0.9:1 to about 1.1:1, more preferably about 1:1. In the preferred sodium salt form, the w:w ratio of hydrogen carbonate:hydroxide is from about 2.5:1 to 2:1, more preferably about 2.3:1, or the ratio of carbonate:hydroxide is from about 2.9:1 to 2.4:1, more preferably about 2.65:1.

In buffers comprising hydrogen carbonate anions and carbonate anions, the molar ratio of hydrogen carbonate:carbonate is about 0.15:1 to about 0.25:1, more preferably about 0.18:1. In the preferred sodium salt form, the w:w ratio of hydrogen carbonate:carbonate is from about 0.1:1 to about 0.2:1, more preferably about 0.14:1.

Although the term "buffer" is used, it is important to understand that the components need not form a true buffer system—The important consideration is the adjustment of the peroxyacetic acid to a pH of between 6.3 and 6.8 in the final working solution. It has been found that the buffer is most advantageously added in an amount to keep the pH between 5.5 and pH 7 and if possible around 6-6.5.

Surprisingly, the present applicant has found that the biocidal activity of peroxyacetic acid, even against spores, is potentiated by the presence of a surfactant. This is the case even at very low concentrations. This effect is also observed to take place in solutions that are adjusted to physiological pH's.

It is surprising that the presence of a surfactant can also increase the biocidal efficacy of such disinfectant solutions.

The effects of adding a wide range of surfactants to buffered peracetic acid were tested against *B. subtilis*.

Amine oxide surfactants tested included cocamidopropylamine oxide ($RCONH(CH_2)_3N(CH_2)_2\rightarrow O$) where R is a cocoalkyl group; dodecyldimethylamine oxide ($C_{14}H_{31}N\rightarrow O$); (($CH_2)_{13}(CH_2)_2N\rightarrow O$); or (($CH_2)_{12-18}(CH_2)_2N\rightarrow O$).

Non-ionic surfactants tested included Triton X-100, (polyethylene glycol p-(1,1,3,3-tetramethylbutyl)-phenyl ether) or Tween-80 (polyethlyene (20) sorbitan monooleate).

Cationic surfactants tested included quaternary ammonium compounds such as benzalkonium chloride or hexadecylpyridinium bromide.

Phosphate ester based anionic surfactants tested included polyoxyethylene alkyl ether phosphates, such as those sold by Croda under the trade name Monafax M1214 or Multitrope 1214; phosphate esters (mono- and/or diester of phosphoric acid with aliphatic alcohols of chain length $C_1$-$C_{22}$ and/or aliphatic diols and/or aliphatic polyols of chain length $C_2$-$C_{22}$) such as Hordaphos 1306 or Hordaphos MDGB from Clariant, which is a diester of phosphoric acid with butanol and ethylene glycol respectively; and Excellene T5 NF which is a blend of ethylhexylphosphate ester and alcohol ethoxylate phosphate ester potassium salts, available from Whewell chemical manufacturers.

The surfactants were mainly, but not in every case, tested in combination with a phosphate buffer. The exact concentrations of peracetic acid, pH, and initial populations of *B. subtilis* were not standardised across the whole range of surfactants tested, so it is not possible to state quantified relative efficacies. However, each surfactant was tested against an appropriate control system (differing only in the absence of the surfactant) so it is possible to conclusively state that in every case an increased efficacy was noted when a surfactant was added. The results of the study were not optimised.

A particularly preferred class of surfactants which gave improved performance were phosphate based anionic surfactants, particularly polyoxyethylene alkyl ether phosphates, such as those sold by Croda under the trade name Monafax M1214 or Multitrope 1214. The results for this class of compound were investigated further and are shown in the examples below.

EXAMPLES

Test Method

The test method employed and described below is typical of all the test methodology used in the present invention to determine biological loads.

The working solution was tested against spores of the appropriate organism at room temperature. Media was TSB+1% Na-thiosulfate+10% Tween 80+1 ml Catalase.

The test method involved taking a 9 ml sample and adding 1 ml culture (with 5% horse serum) and then incubating at the desired temperature if necessary. 1 ml of the incubated sample was then removed at each time point and neutralized with 9 ml neutralizer. The resultant was diluted with saline, plated out and the plates incubated at 37° C. for 48 hr. The results were then able to be expressed in terms of a log reduction. As is usual in the art, a log reduction is a $log_{10}$ reduction. A 4 log reduction means 1 in $10^4$ organisms survived, 5 log reduction corresponds to 1 in $10^5$ organisms surviving and so on. High level disinfection is widely defined and understood as a reduction of 6 log or greater, than is, no more than 1 in 1,000,000 microorganisms survives the process.

Results

Table 1 shows the biocidal effect against *Bacillus subtilis* spores achieved by adding a surfactant to a pH controlled aqueous peracetic acid solution (0.2%) that contained also acetic acid and hydrogen peroxide. It can be seen that the addition of the surfactant had only a very minimal effect upon the pH of the solution, only changing it by around 0.0 to 0.5 pH units.

However, the effect upon the biocidal efficacy was quite dramatic. The addition of just 0.25% surfactant led to between an increase in biocidal efficacy of between 1 and 1.6 $log_{10}$, that is, the surfactant increased the efficacy of peracetic acid by between 10 and about 40-fold.

Table 2 illustrates similar experiments to those in table 1, with the exception that the wt % of peroxy acetic acid was reduced to 0.1%. The surfactant at 0.30% did not exert any adverse effect upon the pH of the mixture.

However, the effect upon the biocidal efficacy was still quite significant. The addition of 0.30% surfactant led to between an increase in biocidal efficacy of between 0.4 and 0.9 $log_{10}$, that is, the surfactant increased the efficacy of peracetic acid by between 3 and about 8-fold.

Table 3 shows the biocidal effect against *Candida albicans* spores obtained by adding a surfactant to a pH controlled aqueous peracetic acid solution (0.05%) that contained also acetic acid and hydrogen peroxide. It can be seen that the addition of the surfactant had only a very minimal effect upon the pH of the solution, changing it from around 0.0 to 0.5 pH units.

Again, the effect upon the biocidal efficacy was quite dramatic. The addition of just 0.23% surfactant led to between an increase in biocidal efficacy of between 0.7 and 1.6 $log_{10}$, that is, the surfactant increased the efficacy of peracetic acid by between 5 and about 40-fold.

Table 4 shows the fungicidal effect against *Aspergillus niger* of adding a surfactant to a pH controlled aqueous peracetic acid solution (0.2%) that contained also acetic acid and hydrogen peroxide. It can be seen that the addition of the surfactant had only a very minimal effect upon the pH of the solution.

However the effect upon the fungicidal efficacy was quite dramatic. The addition of just 0.30% surfactant led to between an increase in biocidal efficacy of between 0.5 and 0.9 $log_{10}$, that is, the surfactant increased the efficacy of peracetic acid by between 3 and about 8-fold.

In summary, a surprising increase in the efficacy of peroxy acetic acid was achieved by the addition of a surfactant. Surfactants are well known not to have any significant biocidal activity in their own right.

TABLE 1

Sporicidal efficacy of biocides on the base of peroxyacetic acid against
*Bacillus subtilis* spores (ATCC 19659) at room temperature (suspension test)

| Compo-sition | Ingredient | Wt % of ingredient | pH of working solution without Surfactant | pH of working solution with 0.25% Surfactant* | Exposure time (min) | $Log_{10}$ Reduction without Surfactant | $Log_{10}$ Reduction with 0.25% Surfactant* |
|---|---|---|---|---|---|---|---|
| I | peroxyacetic acid | 0.2 | 6.56 | 6.51 | 3 | 4.7 | 5.7 |
|  | acetic acid | 0.3 |  |  |  |  |  |
|  | $H2O2$ | 1 |  |  |  |  |  |
|  | phosphate buffer |  |  |  |  |  |  |
| II | peroxyacetic acid | 0.2 | 6.57 | 6.53 | 3 | 5.5 | 5.6 |
|  | acetic acid | 0.3 |  |  |  |  |  |
|  | $H2O2$ | 1 |  |  |  |  |  |
|  | basic buffer (NaOH) |  |  |  |  |  |  |
| III | peroxyacetic acid | 0.2 | 6.52 | 6.52 | 3 | 5.0 | 6.2 |
|  | acetic acid | 0.3 |  |  |  |  |  |
|  | $H2O2$ | 1 |  |  |  |  |  |
|  | carbonate buffer I ($NaHCO_3$ + NaOH) |  |  |  |  |  |  |
| IV | peroxyacetic acid | 0.2 | 6.52 | 6.50 | 3 | 4.7 | 6.2 |
|  | acetic acid | 0.3 |  |  |  |  |  |
|  | $H2O2$ | 1 |  |  |  |  |  |
|  | carbonate buffer II ($Na_2CO_3$ + $NaHCO_3$) |  |  |  |  |  |  |

*Surfactant was Monafax M1214 which also contained 0.01% Antifoaming component AF 86/013 (from Basildon Chemical Company Ltd)

TABLE 2

Sporicidal efficacy of biocides on the base of peroxyacetic acid against
*Bacillus subtilis* spores (ATCC 19659) at room temperature (suspension test)

| Compo-sition | Ingredient | Wt % of ingredient | pH of working solution without Surfactant | pH of working solution with 0.30% Surfactant* | Exposure time (min) | $Log_{10}$ Reduction without Surfactant | $Log_{10}$ Reduction with 0.30% Surfactant* |
|---|---|---|---|---|---|---|---|
| I | peroxyacetic acid | 0.1 | 6.40 | 6.39 | 5 | 1.4 | 1.8 |
|  | acetic acid | 0.15 |  |  |  |  |  |
|  | $H2O2$ | 0.05 |  |  |  |  |  |
|  | phosphate buffer |  |  |  |  |  |  |
| II | peroxyacetic acid | 0.1 | 6.45 | 6.41 | 5 | 1.1 | 1.7 |
|  | acetic acid | 0.15 |  |  |  |  |  |
|  | $H2O2$ | 0.05 |  |  |  |  |  |
|  | basic buffer (NaOH) |  |  |  |  |  |  |
| III | peroxyacetic acid | 0.1 | 6.41 | 6.41 | 5 | 1.5 | 2.4 |
|  | acetic acid | 0.15 |  |  |  |  |  |
|  | $H2O2$ | 0.05 |  |  |  |  |  |
|  | carbonate buffer I ($NaHCO_3$ + NaOH) |  |  |  |  |  |  |
| IV | peroxyacetic acid | 0.1 | 6.44 | 6.39 | 5 | 1.5 | 2.4 |
|  | acetic acid | 0.15 |  |  |  |  |  |
|  | $H2O2$ | 0.05 |  |  |  |  |  |
|  | carbonate buffer II ($Na_2CO_3$ + $NaHCO_3$) |  |  |  |  |  |  |

*Surfactant was Monafax M1214 which also contained 0.01% Antifoaming component AF 86/013 (from Basildon Chemical Company Ltd)

TABLE 3

Biocidal efficacy of biocides on the base of peroxyacetic acid against
*Candida albicans* (ATCC 10231) at room temperature (suspension test)

| Compo-sition | Ingredient | Wt % of ingredient | pH of working solution without Surfactant | pH of working solution with 0.23% Surfactant* | Exposure time (min) | $Log_{10}$ Reduction without Surfactant | $Log_{10}$ Reduction with 0.23% Surfactant* |
|---|---|---|---|---|---|---|---|
| I | peroxyacetic acid | 0.05 | 6.60 | 6.58 | 0.5 | 5.3 | 6.9 |
|  | acetic acid | 0.075 |  |  |  |  |  |

TABLE 3-continued

Biocidal efficacy of biocides on the base of peroxyacetic acid against
*Candida albicans* (ATCC 10231) at room temperature (suspension test)

| | | | pH of working solution | | | Log$_{10}$ Reduction | |
|---|---|---|---|---|---|---|---|
| Composition | Ingredient | Wt % of ingredient | without Surfactant | with 0.23% Surfactant* | Exposure time (min) | without Surfactant | with 0.23% Surfactant* |
| | H2O2 | 0.025 | | | | | |
| | phosphate buffer | | | | | | |
| II | peroxyacetic acid | 0.05 | 6.60 | 6.56 | 0.5 | 5.4 | 6.9 |
| | acetic acid | 0.075 | | | | | |
| | H2O2 | 0.025 | | | | | |
| | basic buffer (NaOH) | | | | | | |
| III | peroxyacetic acid | 0.05 | 6.53 | 6.55 | 0.5 | 5.8 | 6.9 |
| | acetic acid | 0.075 | | | | | |
| | H2O2 | 0.025 | | | | | |
| | carbonate buffer I (NaHCO$_3$ + NaOH) | | | | | | |
| IV | peroxyacetic acid | 0.05 | 6.52 | 6.55 | 0.5 | 6.2 | 6.9 |
| | acetic acid | 0.075 | | | | | |
| | H2O2 | 0.025 | | | | | |
| | carbonate buffer II (Na$_2$CO$_3$ + NaHCO$_3$) | | | | | | |

*Surfactant was Monafax M1214 which also contained 0.01% Antifoaming component AF 86/013 (from Basildon Chemical Company Ltd)

TABLE 4

Fungicidal efficacy of biocides on the base of peroxyacetic acid against
*Aspergillus niger* (ATCC 16404) at room temperature (suspension test)

| | | | pH of working solution | | | Log$_{10}$ Reduction | |
|---|---|---|---|---|---|---|---|
| Composition | Ingredient | Wt % of ingredient | without Surfactant | with 0.30% Surfactant* | Exposure time (min) | without Surfactant | with 0.30% Surfactant* |
| I | peroxyacetic acid | 0.1 | 6.16 | 6.16 | 2 | 1.0 | 1.9 |
| | acetic acid | 0.15 | | | | | |
| | H2O2 | 0.05 | | | | | |
| | phosphate buffer | | | | | | |
| II | peroxyacetic acid | 0.1 | 6.25 | 6.13 | 2 | 0.9 | 1.4 |
| | acetic acid | 0.15 | | | | | |
| | H2O2 | 0.05 | | | | | |
| | basic buffer (NaOH) | | | | | | |
| III | peroxyacetic acid | 0.1 | 6.13 | 6.21 | 2 | 1.2 | 2.1 |
| | acetic acid | 0.15 | | | | | |
| | H2O2 | 0.05 | | | | | |
| | carbonate buffer I (NaHCO$_3$ + NaOH) | | | | | | |
| IV | peroxyacetic acid | 0.1 | 6.24 | 6.18 | 2 | 1.9 | 2.6 |
| | acetic acid | 0.15 | | | | | |
| | H2O2 | 0.05 | | | | | |
| | carbonate buffer II (Na$_2$CO$_3$ + NaHCO$_3$) | | | | | | |

*Surfactant was Monafax M1214 which also contained 0.01% Antifoaming component AF 86/013 (from Basildon Chemical Company Ltd)

The claims of the invention are as follows:

1. An aqueous disinfectant solution comprising:
   0.1 to 0.3 wt % of peroxyacetic acid;
   hydrogen peroxide; and
   0.23 to 0.3 wt % of a surfactant; and
   wherein the solution has a pH in the range of 6-7.

2. An aqueous disinfectant solution according to claim 1 further comprising acetic acid and wherein the solution has a pH in the range of 6-6.5.

3. An aqueous disinfectant solution according to claim 2 wherein the surfactant is selected from the group consisting of polyoxyethylene alkyl ether phosphates, polyethylene glycol p-(1,1,3,3-tetramethylbutyl)-phenyl ether and cocoamidopropylamino oxide.

4. An aqueous disinfectant solution according to claim 1 wherein the solution is adjusted to provide a pH in the range of 6-7 by a pH adjusting agent selected from the group consisting of a phosphate buffer; hydroxide; carbonate; bicarbonate; a combination of carbonate and hydroxide; and a combination of carbonate and bicarbonate.

5. An aqueous disinfectant solution according claim 4 wherein the surfactant is selected from the group consisting of polyoxyethylene alkyl ether phosphates, polyethylene glycol p-(1,1,3,3-tetramethylbutyl)-phenyl ether and cocoamidopropylamino oxide.

6. An aqueous disinfectant solution according to claim 1 wherein the ratio of hydrogen peroxide:peroxyacetic acid is 5:1 or greater.

7. An aqueous disinfectant solution according claim 6 wherein the surfactant is selected from the group consisting of polyoxyethylene alkyl ether phosphates, polyethylene glycol p-(1,1,3,3-tetramethylbutyl)-phenyl ether and cocoamidopropylamino oxide.

8. An aqueous disinfectant solution according to claim 1 wherein the ratio of hydrogen peroxide:peroxyacetic acid is 10:1 or greater.

9. An aqueous disinfectant solution according to claim 1 wherein the ratio of hydrogen peroxide:peroxyacetic acid is 15:1 or greater.

10. An aqueous disinfectant solution according to claim 1 wherein the ratio of hydrogen peroxide:peroxyacetic acid is 30:1 or greater.

11. An aqueous disinfectant solution according claim 10 wherein the surfactant is selected from the group consisting of polyoxyethylene alkyl ether phosphates, polyethylene glycol p-(1,1,3,3-tetramethylbutyl)-phenyl ether and cocoamidopropylamino oxide.

12. An aqueous disinfectant solution according to claim 1 wherein the surfactant is a non-ionic surfactant.

13. An aqueous disinfectant solution according claim 1 wherein the surfactant is selected from the group consisting of polyoxyethylene alkyl ether phosphates, polyethylene glycol p-(1,1,3,3-tetramethylbutyl)-phenyl ether and cocoamidopropylamino oxide.

14. An aqueous disinfectant solution according to claim 1 wherein the surfactant is a polyoxyethylene alkyl ether phosphate.

15. An aqueous disinfectant solution according to claim 1 further including a corrosion inhibitor.

16. An aqueous disinfectant solution according to claim 15 wherein the corrosion inhibitor is a benzotriazole.

17. An aqueous disinfectant solution according claim 15 wherein the surfactant is selected from the group consisting of polyoxyethylene alkyl ether phosphates, polyethylene glycol p-(1,1,3,3-tetramethylbutyl)-phenyl ether and cocoamidopropylamino oxide.

18. An aqueous disinfectant solution according to claim 1 further including an antifoaming agent.

19. An aqueous disinfectant solution according claim 18 wherein the surfactant is selected from the group consisting of polyoxyethylene alkyl ether phosphates, polyethylene glycol p-(1,1,3,3-tetramethylbutyl)-phenyl ether and cocoamidopropylamino oxide.

20. An aqueous disinfectant solution according to claim 1, wherein hydrogen peroxide is present in an amount ranging from 0.05 to 1 wt % of the composition.

21. An aqueous disinfectant solution comprising:
    0.1 to 0.3 wt % of peroxyacetic acid;
    hydrogen peroxide; and
    0.23 to 0.3 wt % of a surfactant selected from the group consisting of amine oxide surfactants, quaternary ammonium surfactants, and polyoxyethylene alkyl ether phosphates; and
    wherein the solution has a pH in the range of 6-7.

22. An aqueous disinfectant solution according to claim 21, wherein hydrogen peroxide is present in an amount ranging from 0.05 to 1 wt % of the composition.

23. A method of disinfection of an article comprising contacting an article with the aqueous disinfectant solution according to claim 1.

24. A method according to claim 23 wherein the method is carried out in a temperature range of 15-40° C.

25. A method according to claim 23 wherein the method is carried out in a temperature range of 20-35° C.

26. A method according to claim 23 wherein the method is carried out at ambient temperature.

\* \* \* \* \*